US012575756B2

(12) United States Patent
    Tamura et al.

(10) Patent No.: US 12,575,756 B2
(45) Date of Patent: Mar. 17, 2026

(54) MAGNETIC RESONANCE IMAGING APPARATUS, PHASE CORRECTING METHOD, AND IMAGING CONTROLLING METHOD

(71) Applicant: CANON MEDICAL SYSTEMS CORPORATION, Otawara (JP)

(72) Inventors: Takahiro Tamura, Nasushiobara (JP); Mitsuhiro Bekku, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 293 days.

(21) Appl. No.: 18/318,190

(22) Filed: May 16, 2023

(65) Prior Publication Data

US 2023/0397835 A1 Dec. 14, 2023

(30) Foreign Application Priority Data

Jun. 9, 2022 (JP) ................................. 2022-093667

(51) Int. Cl.
    *A61B 5/055* (2006.01)
    *A61B 5/00* (2006.01)
    (Continued)

(52) U.S. Cl.
    CPC ............ *A61B 5/055* (2013.01); *G06T 7/0002* (2013.01); *G16H 30/40* (2018.01); *A61B 5/0033* (2013.01); *G06T 2207/10088* (2013.01)

(58) Field of Classification Search
    CPC ...... A61B 5/055; A61B 5/0033; G16H 30/40; G06T 7/0002; G06T 2207/10088
    See application file for complete search history.

(56) References Cited

U.S. PATENT DOCUMENTS

2019/0033418 A1 * 1/2019 Haacke ................. A61B 5/055
2020/0007463 A1   1/2020 Kleyn et al.
                  (Continued)

FOREIGN PATENT DOCUMENTS

JP      S64-076843 A     3/1989
JP      2001-000414 A    1/2001
                  (Continued)

OTHER PUBLICATIONS

Applications of the Dixon technique in the evaluation of the musculoskeletal system, Lins et al.; (Year: 2019).*
                  (Continued)

*Primary Examiner* — Ming Shui
(74) *Attorney, Agent, or Firm* — Oblon, McClelland, Maier & Neustadt, L.L.P.

(57) ABSTRACT

A MRI apparatus according to an embodiment includes processing circuitry. The processing circuitry obtains MR data acquired by implementing an IR method under a condition where a phase difference in a complex signal related to observed elements is equal to π, due to a difference in longitudinal magnetization relaxation time between the observed elements; generates phase data on the basis of the MR data; multiplies a phase angle in the phase data by 2n; unfolds the phase of phase data having the phase angle multiplied by 2n; multiplies the phase angle in the unfolded phase data by 1/(2n); generates a phase correction map used for correcting a phase with respect to the complex signal, by applying a complex conjugate to phase data having the phase angle multiplied by 1/(2n); and performs a phase correction on the MR data by using the phase correction map.

4 Claims, 7 Drawing Sheets

(51)  Int. Cl.
     *G06T 7/00*      (2017.01)
     *G16H 30/40*    (2018.01)

(56)            References Cited

U.S. PATENT DOCUMENTS

| | | | |
|---|---|---|---|
| 2020/0074635 | A1 | 3/2020 | Satoh et al. |
| 2020/0309887 | A1* | 10/2020 | Bekku .............. G01R 33/56563 |
| 2020/0309984 | A1* | 10/2020 | Pan .......................... G01V 3/28 |

FOREIGN PATENT DOCUMENTS

| | | |
|---|---|---|
| JP | 2012-065736 A | 4/2012 |
| JP | 2015-116474 A | 6/2015 |
| JP | 2020-31848 A | 3/2020 |

OTHER PUBLICATIONS

Japanese Office Action dated Dec. 23, 2025, issued in Japanese Application No. 2022-096667 (with English translation).

* cited by examiner

FIRST MULTIPLYING PROCESS

MAGNETIC RESONANCE IMAGING APPARATUS, PHASE CORRECTING METHOD, AND IMAGING CONTROLLING METHOD

CROSS-REFERENCE TO RELATED APPLICATIONS

This application is based upon and claims the benefit of priority from Japanese Patent Application No. 2022-093667, filed on Jun. 9, 2022, the entire contents of which are incorporated herein by reference.

FIELD

Embodiments described herein relate generally to a magnetic resonance imaging apparatus, a phase correcting method, and an imaging controlling method.

BACKGROUND

Conventionally, magnetic resonance imaging apparatuses may generate a real image depending on observed elements. In those situations, a phase correction is carried out at the time of generating the real image, in order to reduce black/white signal unevenness in the real image. For the phase correction, a template image generated in a preliminary imaging process may be used. In that situation, the imaging period may be prolonged. Further, another technique is also known by which a phase correction is performed without using a template image. In that situation, however, even after the phase correction is performed, impacts of the signal unevenness may remain in the real image depending on observed elements. Further, for this technique, a method is known by which the impacts of the signal unevenness in the real image are reduced by performing a phase correction while masking a region having a strong negative signal in the real image. However, optimizing a setting of a threshold value for the masking process or the like is difficult.

DETAILED DESCRIPTION

Figure 1:
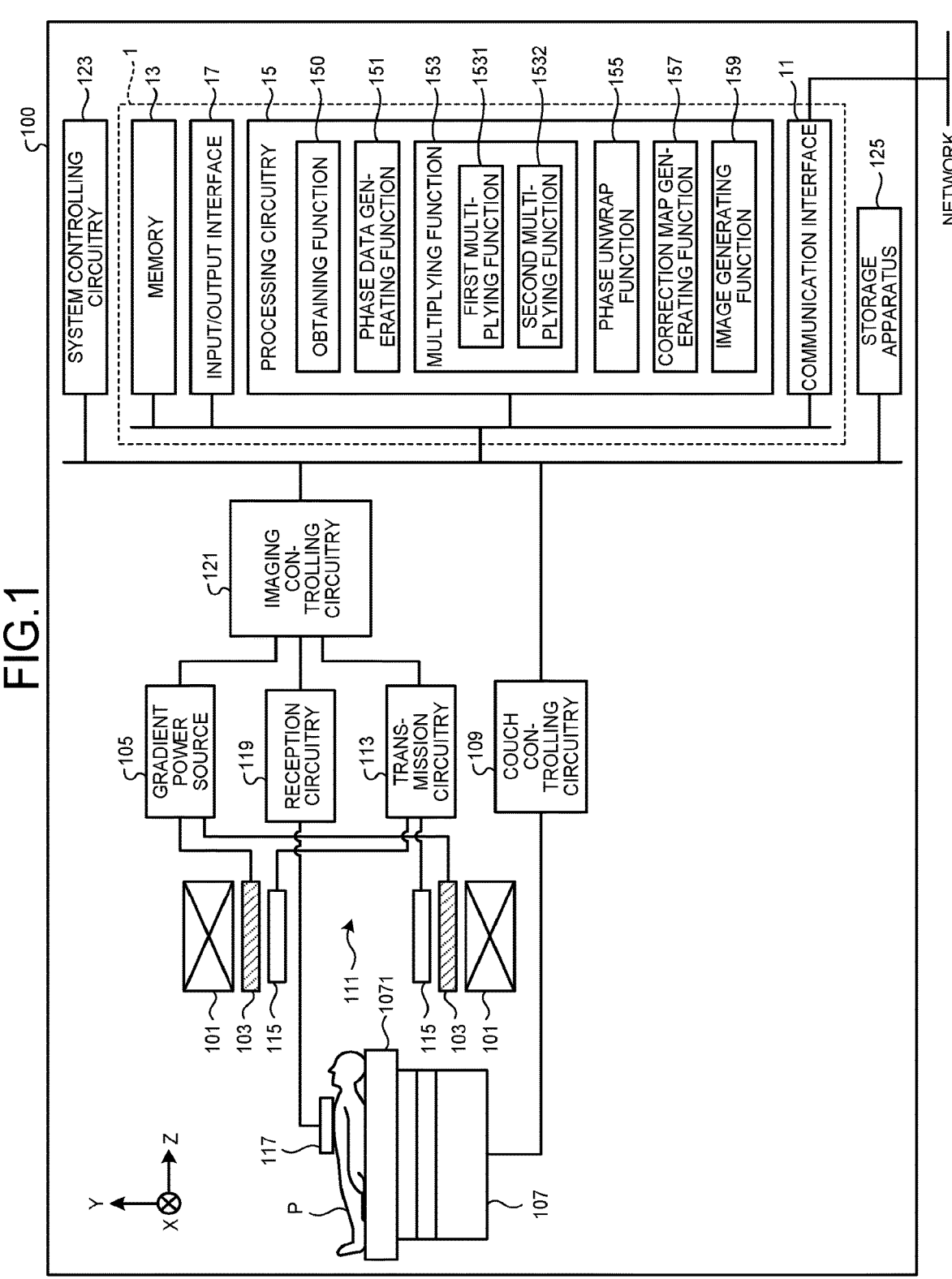
FIG. 1 is a block diagram illustrating an example of a magnetic resonance imaging apparatus according to an embodiment.

A magnetic resonance imaging apparatus according to an embodiment includes processing circuitry. The processing circuitry is configured: to obtain magnetic resonance data acquired by implementing an inversion recovery method under a condition where a phase difference in a complex signal related to two or more observed elements is equal to π, due to a difference in longitudinal magnetization relaxation time between the two or more observed elements; to generate at least phase data on the basis of the magnetic resonance data; to multiply a phase angle in the phase data by 2n (where n is a natural number); to unfold the phase of phase data having the phase angle multiplied by 2n; to multiply the phase angle in the unfolded phase data by $1/(2n)$; to generate a phase correction map used for correcting a phase with respect to the complex signal, by applying a complex conjugate to phase data having the phase angle multiplied by $1/(2n)$; and to perform a phase correction on the magnetic resonance data by using the phase correction map.

Exemplary embodiments of a magnetic resonance imaging apparatus and a phase correcting method will be explained below, with reference to the accompanying drawings. In the following embodiments, some of the elements that are referred to by using the same reference characters are assumed to perform the same operations, and duplicate explanations thereof will be omitted. Functions described in the embodiments do not necessarily have to be realized by a Magnetic Resonance Imaging (hereinafter, "MRI") apparatus and may be realized by a Positron Emission Tomography (PET)-MRI apparatus or a Single Photon Emission Computed Tomography (SPECT)-MRI apparatus, for example.

Embodiments

FIG. 1 is a diagram illustrating an example of an MRI apparatus 100 according to an embodiment of the present disclosure. As illustrated in FIG. 1, the MRI apparatus 100 includes a static magnetic field magnet 101, a gradient coil 103, a gradient power source 105, a couch 107, couch controlling circuitry (a couch controlling unit) 109, transmission circuitry 113, a transmission coil 115, a reception coil 117, reception circuitry 119, imaging controlling circuitry (an acquiring unit) 121, system controlling circuitry (a system controlling unit) 123, a storage apparatus 125, and an image processing apparatus 1.

The static magnetic field magnet 101 is a magnet formed to have a hollow and substantially circular cylindrical shape. The static magnetic field magnet 101 is configured to generate a substantially uniform static magnetic field in the space inside thereof. For example, a superconductive magnet or the like may be used as the static magnetic field magnet 101.

The gradient coil 103 is a coil formed to have a hollow and substantially circular cylindrical shape and is arranged on the inner surface side of a circular cylindrical cooling container. By individually receiving electric current supplies from the gradient power source 105, the gradient coil 103 is configured to generate gradient magnetic fields of which magnetic field intensities change along X-, Y-, and Z-axes that are orthogonal to one another. The gradient magnetic fields generated along the X-, Y-, and Z-axes by the gradient coil 103 form, for example, a slice selecting gradient magnetic field, a phase encoding gradient magnetic field, and a frequency encoding gradient magnetic field (which may be referred to as a readout gradient magnetic field). The slice selecting gradient magnetic field is used for arbitrarily determining an imaged cross-sectional plane. The phase encoding gradient magnetic field is used for changing the phase of a magnetic resonance signal (hereinafter, "MR signal") in accordance with spatial positions. The frequency encoding gradient magnetic field is used for changing the frequency of an MR signal in accordance with spatial positions.

The gradient power source 105 is a power source apparatus configured to supply the electric currents to the gradient coil 103 under control of the imaging controlling circuitry 121.

The couch 107 is an apparatus provided with a couchtop 1071 on which an examined subject (hereinafter, "patient") P is placed. The couch 107 is configured to insert the couchtop 1071 on which the patient P is placed, into a bore 111, under control of the couch controlling circuitry 109. The couch controlling circuitry 109 is circuitry configured to control the couch 107. The couch controlling circuitry 109 is configured to move the couchtop 1071 in longitudinal directions and up-and-down directions, as well as left-and-right directions in some situations, by driving the couch 107 according to instructions received from an operator via an input/output interface 17.

The transmission circuitry 113 is configured to supply a radio frequency pulse modulated with a Larmor frequency to the transmission coil 115, under control of the imaging controlling circuitry 121. For example, the transmission circuitry 113 includes an oscillating unit, a phase selecting unit, a frequency converting unit, an amplitude modulating unit, a Radio Frequency (RF) amplifier, and the like. The oscillating unit is configured to generate an RF pulse at a resonance frequency unique to targeted atomic nuclei placed in the static magnetic field. The phase selecting unit is configured to select a phase of the RF pulse generated by the oscillating unit. The frequency converting unit is configured to convert the frequency of the RF pulse output from the phase selecting unit. The amplitude modulating unit is configured to modulate the amplitude of the RF pulse output from the frequency converting unit, according to a sinc function, for example. The RF amplifier is configured to amplify the RF pulse output from the amplitude modulating unit and to supply the amplified RF pulse to the transmission coil 115.

The transmission coil 115 is a Radio Frequency (RF) coil arranged on the inside of the gradient coil 103. The transmission coil 115 is configured to generate an RF pulse corresponding to a radio frequency magnetic field in accordance with the output of the transmission circuitry 113.

The reception coil 117 is an RF coil arranged on the inside of the gradient coil 103. The reception coil 117 is configured to receive an MR signal emitted from the patient P, due to the radio frequency magnetic field. The reception coil 117 is configured to output the received MR signal to the reception circuitry 119. For example, the reception coil 117 is a coil array including one or more (typically two or more) coil elements. In the following sections, to explain a specific example, it will be assumed that the reception coil 117 is a coil array including a plurality of coil elements.

Alternatively, the reception coil 117 may be configured with one coil element. Further, although FIG. 1 illustrates the example in which the transmission coil 115 and the reception coil 117 are separate RF coils, the transmission coil 115 and the reception coil 117 may be embodied as an integrally-formed transmission/reception coil. The transmission/reception coil corresponds to an imaged site of the patient P and is a local transmission/reception RF coil such as a head coil, for example.

Under control of the imaging controlling circuitry 121, the reception circuitry 119 is configured to generate magnetic resonance data (hereinafter, "MR data") represented by a digital MR signal, on the basis of the MR signal output from the reception coil 117. More specifically, the reception circuitry 119 is configured to generate the MR data, by performing various types of signal processing processes on the MR signal output from the reception coil 117 and subsequently performing an Analog-to-Digital (A/D) conversion on the data resulting from the various types of signal processing processes. The reception circuitry 119 is configured to output the generated MR data to the imaging controlling circuitry 121. For example, the MR data is generated for each of the coil elements and is output to the imaging controlling circuitry 121 together with a tag identifying a corresponding one of the coil elements.

The imaging controlling circuitry 121 is configured to perform an imaging process on the patient P, by controlling the gradient power source 105, the transmission circuitry 113, the reception circuitry 119, and the like, according to an image taking protocol output from processing circuitry 15.

The image taking protocol includes a pulse sequence corresponding to the type of a medical examination. The image taking protocol defines: a magnitude of the electric current to be supplied by the gradient power source 105 to the gradient coil 103; timing with which the electric current is to be supplied by the gradient power source 105 to the gradient coil 103; a magnitude and a time width of the radio frequency pulse to be supplied by the transmission circuitry 113 to the transmission coil 115; timing with which the radio frequency pulse is to be supplied by the transmission circuitry 113 to the transmission coil 115; timing with which the MR signal is to be received by the reception coil 117; and the like. When having received the MR data from the reception circuitry 119, as a result of imaging the patient P by driving the gradient power source 105, the transmission circuitry 113, the reception circuitry 119, and the like, the imaging controlling circuitry 121 is configured to transfer the received MR data to the image processing apparatus 1, or the like.

The imaging controlling circuitry 121 is realized by using a processor, for example. The imaging controlling circuitry 121 corresponds to an imaging controlling unit. For example, the imaging controlling circuitry 121 is configured to execute a pulse sequence having a condition (hereinafter "π condition") where a phase difference in a complex signal related to two or more observed elements in the patient P is equal to π, due to a difference in longitudinal magnetization relaxation time T1 between the two or more observed elements. More specifically, the imaging controlling circuitry 121 is configured to execute a magnetic resonance imaging process on the patient P, according to the pulse sequence implementing an Inversion Recovery (hereinafter, "IR") method under the π condition. Thus, the imaging controlling circuitry 121 is configured to acquire the MR data by implementing the IR method under the π condition.

In the following sections, to explain specific examples, it is assumed that the observed elements are, for instance, cerebrospinal fluid (hereinafter, "CSF") and white matter (hereinafter, "WM"). However, possible observed elements are not limited to these examples and may be, for instance, CSF and grey matter (GM); a normal myocardium and a damaged myocardium; WM, GM, and fat; or the like. For instance, in the examples of a normal myocardium and a damaged myocardium or WM, GM, and fat, an imaging process may be executed according to a sequence implementing a Phase Sensitive Inversion Recovery (PSIR) method under the $\pi$ condition.

Figure 2:
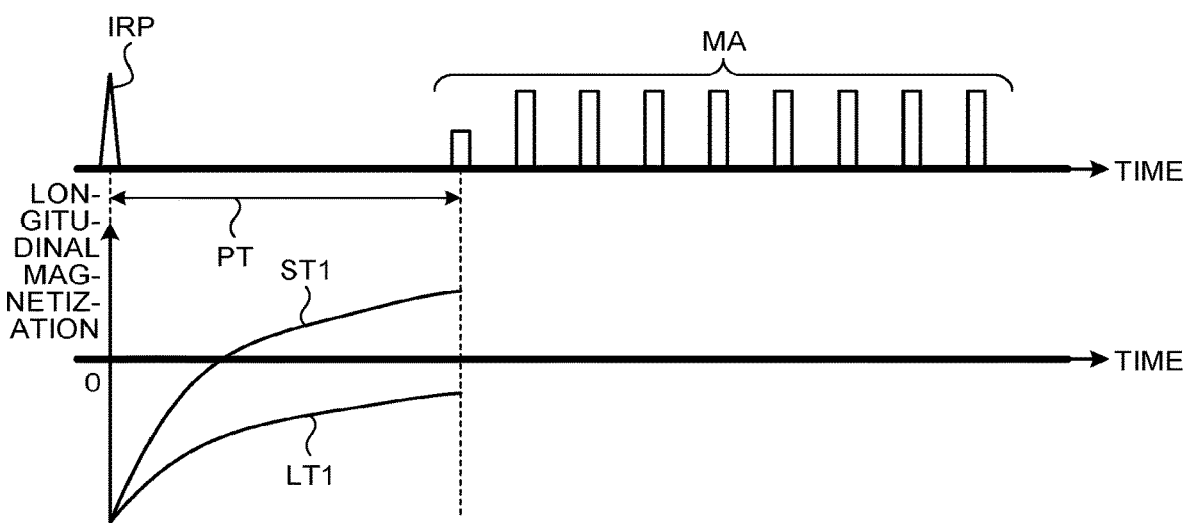
FIG. 2 is a drawing illustrating an example of a pulse sequence according to the embodiment.

FIG. 2 is a drawing illustrating an example of a pulse sequence executed in the present embodiment. As illustrated in FIG. 2, when a prescribed time period PT has elapsed since application of an inversion pulse IRP, an MR data acquisition MA is performed. In FIG. 2, of the two curves (ST1 and LT1) indicating temporal changes of the magnetization, the curve ST1 exhibits relaxation time T1 shorter than that of the curve LT1. The observed element corresponding to the curve ST1 may be CSF, for example. The observed element corresponding to the curve LT1 may be WM, for example. In this situation, the prescribed time period PT is set in advance according to the $\pi$ condition where a phase difference in a complex signal related to CSF and WM is equal to $\pi$, due to the difference in the longitudinal magnetization relaxation time T1 related to CSF and WM. As a result of executing the pulse sequence illustrated in FIG. 2, the imaging controlling circuitry 121 is configured to acquire the MR data. The acquired MR data is stored into a memory 13.

In the description above, the example was explained in which a "processor" is configured to read and execute programs corresponding to functions from the memory 13.

However, possible embodiments are not limited to this example. For instance, the term "processor" denotes, for example, a Central Processing Unit (CPU), a Graphics Processing Unit (GPU), or circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)).

For example, when the processor is a CPU, the processor is configured to realize the functions by reading and executing the programs saved in the memory 13. In contrast, when the processor is an ASIC, instead of having the programs saved in the memory 13, the functions are directly incorporated in the circuitry of the processor as logic circuitry. Further, processors of the present embodiments do not each necessarily have to be structured as a single piece of circuitry. It is also acceptable to structure one processor by combining together a plurality of pieces of independent circuitry, so as to realize the functions thereof. Further, although the example was explained in which the single piece of storage circuitry is configured to store therein the programs corresponding to the processing functions, it is also acceptable to provide a plurality of pieces of storage circuitry in a distributed manner, so that the processing circuitry reads a corresponding program from each of the individual pieces of storage circuitry.

The system controlling circuitry 123 includes, as hardware resources thereof, a processor as well as memory elements such as a Read-Only Memory (ROM), a Random Access memory (RAN), and/or the like (not illustrated) and is configured to control the MRI apparatus 100 by employing a system controlling function. More specifically, the system controlling circuitry 123 is configured to read a system controlling program stored in the storage apparatus 125 so as to be loaded into a memory and configured to control circuitry of the MRI apparatus 100 according to the loaded system controlling program. For example, the system controlling circuitry 123 is configured to read the image taking protocol from the storage apparatus 125 on the basis of an image taking condition input by the operator via the input/output interface 17. The system controlling circuitry

123 is configured to transmit the image taking protocol to the imaging controlling circuitry 121 so as to control the imaging process performed on the patient P. For example, the system controlling circuitry 123 is realized by using a processor. Alternatively, the system controlling circuitry 123 may be incorporated in the processing circuitry 15. In that situation, the system controlling function is executed by the processing circuitry 15, so that the processing circuitry 15 functions as a substitute for the system controlling circuitry 123. The system controlling circuitry 123 corresponds to a system controlling unit.

The storage apparatus 125 is configured to store therein various types of programs to be executed by the system controlling circuitry 123, various types of image taking protocols, image taking conditions including a plurality of image taking parameters defining image taking protocols, and the like. The storage apparatus 125 may be, for example, a semiconductor memory element such as a RAM or a flash memory, a Hard Disk Drive (HDD), a Solid State Drive (SSD), an optical disc, or the like. Further, the storage apparatus 125 may be a Compact Disc Read-Only Memory (CD-ROM) drive, a Digital Versatile Disc (DVD) drive, a drive apparatus configured to read and write various types of information from and to a portable storage medium such as a flash memory, or the like. Alternatively, the data stored in the storage apparatus 125 may be stored in the memory 13. In that situation, the memory 13 functions as a substitute for the storage apparatus 125.

The image processing apparatus 1 includes a communication interface 11, the memory 13, and the processing circuitry 15. As illustrated in FIGS. 1 and 2, in the image processing apparatus 1, the communication interface 11, the memory 13, and the processing circuitry 15 are electrically connected together by a bus. As illustrated in FIGS. 1 and 2, the image processing apparatus 1 is connected to a network via the communication interface 11. The connection to the network makes it possible to communicate, for example, with various types of modalities and one or more information processing systems in the medical institution such as a Hospital Information System (HIS), a Radiology Information System (RIS), and/or the like.

For example, the communication interface 11 is configured to perform data communication with various types of modalities configured to image the patient P during medical examinations performed on the patient P, a Hospital Information System (HIS), a medical image management system which may be called a Picture Archiving and Communication System (PACS), and/or the like. The standard of the communication between the communication interface 11 and the various types of modalities and the hospital information system may be any standard. It is acceptable to use, for example, one or both of Health Level 7 (HL7) and Digital Imaging and Communications in Medicine (DICOM).

The memory 13 is realized by using storage circuitry configured to store therein various types of information. For example, the memory 13 is a storage apparatus such as a Hard Disk Drive (HDD), a Solid State Drive (SSD), or an integrated circuitry storage apparatus. The memory 13 corresponds to a storage unit. Instead of being an HDD or an SSD, the memory 13 may be a semiconductor memory element such as a Random Access memory (RAN) or a flash memory; an optical disc such as a Compact Disc (CD) or a Digital Versatile Disc (DVD); or a drive apparatus configured to read and write various types of information from and to a portable storage medium or a semiconductor memory element such as a RAM.

The memory 13 has stored therein an obtaining function 150, a phase data generating function 151, a multiplying function 153, a phase unwrap function 155, a correction map generating function 157, and an image generating function 159 realized by the processing circuitry 15, in the form of computer-executable programs. The memory 13 is configured to store therein the MR data obtained by the obtaining function 150 from the imaging controlling circuitry 121. Further, the memory 13 is configured to store therein phase data generated by the phase data generating function 151.

Further, the memory 13 is configured to store therein a phase correction map generated by the correction map generating function 157. The phase correction map is a map used for a phase correction to be performed on a complex signal related to a complex image. The memory 13 is configured to store therein the complex image generated by the image generating function 159 on the basis of the MR data. The memory 13 is configured to store therein a phase-corrected complex image in which a phase has been corrected by the image generating function 159. The phase-corrected complex image is a complex image in which the phase has been corrected by the image generating function 159 on the basis of the complex image and the phase correction map. Further, the memory 13 is configured to store therein a real part image generated on the basis of the phase-corrected complex image.

The processing circuitry 15 is configured to control the entirety of the image processing apparatus 1. The processing circuitry 15 is realized by using a processor like the one explained above. The processing circuitry 15 includes the obtaining function 150, the phase data generating function 151, the multiplying function 153, the phase unwrap function 155, the correction map generating function 157, the image generating function 159, and the like. The multiplying function 153 includes a first multiplying function 1531 and a second multiplying function 1532. In other words, the multiplying function 153 has functions realized by the first multiplying function 1531 and the second multiplying function 1532. The obtaining function 150, the phase data generating function 151, the multiplying function 153, the phase unwrap function 155, and the correction map generating function 157 correspond to a pre-processing process for the phase correction performed on the complex image. The processing circuitry 15 realizing the obtaining function 150, the phase data generating function 151, the multiplying function 153, the phase unwrap function 155, the correction map generating function 157, and the image generating function 159 corresponds to an obtaining unit, a phase data generating unit, a multiplying unit, a folding eliminating (unfolding) unit, a correction map generating unit, and an image generating unit, respectively. Further, the processing circuitry 15 realizing the first multiplying function 1531 and the second multiplying function 1532 corresponds to a first multiplying unit and a second multiplying unit, respectively.

Functions such as the obtaining function 150, the phase data generating function 151, the multiplying function 153, the phase unwrap function 155, the correction map generating function 157, and the image generating function 159 are stored in the memory 13 in the form of computer-executable programs. For example, the processing circuitry 15 is configured to realize the functions corresponding to the programs, by reading and executing the programs from the memory 13. In other words, the processing circuitry 15 that has read the programs has the functions such as the obtaining function 150, the phase data generating function 151, the multiplying function 153, the phase unwrap function 155, the correction map generating function 157, and the image generating function 159, or the like.

By employing the obtaining function 150, the processing circuitry 15 is configured to obtain magnetic resonance data acquired by implementing the inversion recovery method under the condition where a phase difference in a complex signal related to two or more observed elements is equal to $\pi$, due to a difference in longitudinal magnetization relaxation time between the two or more observed elements. In this regard, when functions realized by the image processing apparatus 1 are not installed in the MRI apparatus 100, but are installed in an image processing server such as a PACS server or in a cloud, for example, the obtaining function 150 is configured to obtain the MR data acquired by implementing the inversion recovery method under the $\pi$ condition, from an MRI apparatus, an image server, or the like. The obtaining function 150 is configured to store the obtained MR data into the memory 13.

By employing the phase data generating function 151, the processing circuitry 15 is configured to generate at least phase data on the basis of the MR data. More specifically, the phase data generating function 151 is configured to generate the phase data on the basis of a complex image generated by performing a Fourier transform on the MR data. The phase data corresponds to a phase image related to the complex image. The data of each of a plurality of pixels in the phase image indicates a phase angle. Because it is possible to generate the phase image from the complex image by using a known method, explanations thereof will be omitted. Alternatively, the generation of the phase data may be realized by the image generating function 159. In that situation, the functions realized by the phase data generating function 151 would be carried out by the image generating function 159.

Figure 3:
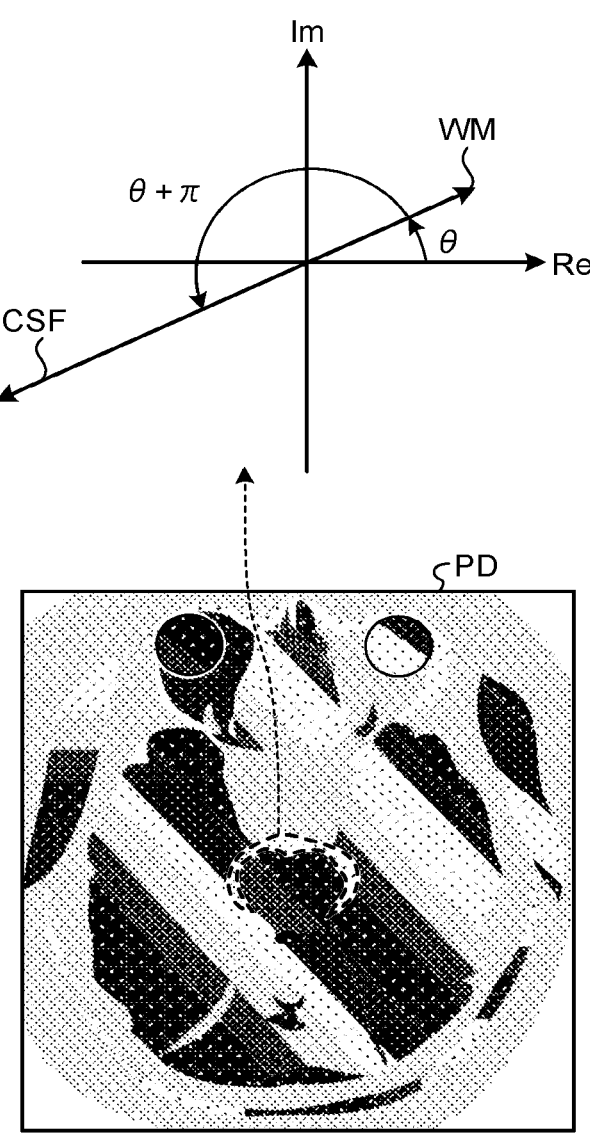
FIG. 3 is a drawing according to the embodiment illustrating an example of phase data and an example of a phase angle formed by cerebrospinal fluid (CSF) and white matter (WM) in the area indicated with the dotted line in the phase data.

FIG. 3 is a drawing illustrating phase data PD and an example of a phase angle formed by CSF and WM in the area indicated with the dotted line in the phase data PD. As illustrated in FIG. 3, when the phase angle of WM is $\theta$, the phase angle of CSF is expressed as "$\theta+\pi$". In other words, WM=exp(i$\theta$)=cos $\theta$+i sin $\theta$ is true. Also, CSF=exp(i($\theta+\pi$)) =cos ($\theta+\pi$)+i sin($\theta+\pi$) is true.

By employing the first multiplying function 1531, the processing circuitry 15 is configured to multiply the phase angles in the phase data by 2n (where n is a natural number). For example, when the phase angle of a pixel (x,y) in the phase image is $\theta$(x,y), the first multiplying function 1531 is configured to generate phase data (hereinafter, "first multiplied phase data") having $2 \times n \times \theta$(x,y), by multiplying the phase angle $\theta$(x,y) by "2$\times$n". More specifically, when the phase data is expressed as exp(i$\theta$(x,y)), the first multiplying function 1531 is configured to raise the phase data to the 2n-th power. In that situation, the first multiplied phase data is expressed as (exp(i$\theta$(x,y)))^(2n)=exp(2ni$\theta$(x,y)). The first multiplying function 1531 is configured to store the first multiplied phase data obtained by multiplying the phase angles in the phase data by 2n, into the memory 13. In the following sections, to explain a specific example, n is assumed to be 1. In that situation, the first multiplying function 1531 is configured to generate the first multiplied phase data expressed as exp(2i$\theta$(x,y)), by squaring the phase data expressed as exp(i$\theta$(x,y)).

Figure 4:
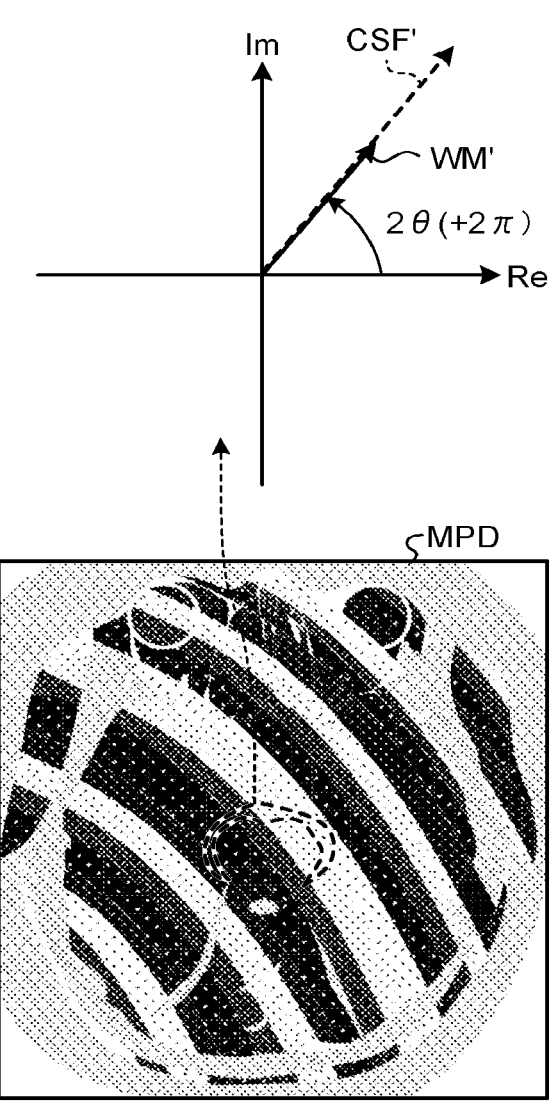
FIG. 4 is a drawing according to the embodiment illustrating an example of first multiplied phase data and an example of a phase angle formed by cerebrospinal fluid (CSF) and white matter (WM) in the area indicated with the dotted line in the first multiplied phase data.

FIG. 4 is a drawing illustrating first multiplied phase data MPD and an example of a phase angle formed by CSF and WM in the area indicated with the dotted line in the first multiplied phase data MPD. As illustrated in FIG. 4, the phase angle of squared white matter WM' (=WM$\times$WM) is equal to 2$\theta$. In other words, WM'=exp(i2$\theta$)=cos 2$\theta$+i sin 2$\theta$ is true. Further, the phase angle of squared cerebrospinal fluid CSF' ($=$CSF$\times$CSF) is expressed as "$2\theta+2\pi$". In other words, CSF'$=\exp(i(2\theta+2\pi))=\exp(i2\theta)\times\exp(2\pi i)=\exp(i2\theta)$ $=\cos(2\theta)+i\sin(2\theta)$ is true. Accordingly, as illustrated in FIG. 4, the squared white matter WM' and the squared cerebrospinal fluid CSF' have the same phase as each other.

By employing the phase unwrap function 155, the processing circuitry 15 is configured to eliminate folding from (hereinafter, "unfold") the phase of the phase data having the phase angles multiplied by 2n. For example, the phase unwrap function 155 is configured to apply a low-pass filter to the first multiplied phase data. By applying the low-pass filter, the phase unwrap function 155 is configured to eliminate a radio frequency component of the first multiplied phase data, i.e., a component that does not contribute to phase changes in general. Subsequently, the phase unwrap function 155 is configured to unfold the phase of the phase data obtained by applying the low-pass filter to the phase data having the phase angles multiplied by 2n. For example, the phase unwrap function 155 is configured to eliminate (dissolve) phase discontinuity at a phase folding point caused by the phase folding. In other words, the phase unwrap process realized by the phase unwrap function 155 is, for example, a process of correcting the values of the phase angles in the part exhibiting the discontinuity so as to be continuous with the values of the phase angles in the vicinity of the folding point. Because the specifics of the processing in the phase unwrap process realized by the phase unwrap function 155 are known, explanations thereof will be omitted.

By employing the second multiplying function 1532, the processing circuitry 15 is configured to multiply the phase angles in the unfolded phase data (hereinafter, "unwrapped phase data") by 1/(2n). When n$=$1 is true, specifically, the second multiplying function 1532 is configured to calculate the square root of the unfolded first multiplied phase data. As a result, the phase angles in the unfolded first multiplied phase data return to the original value $\theta$.

By employing the correction map generating function 157, the processing circuitry 15 is configured to generate a phase correction map used for correcting the phase with respect to a complex signal related to a complex image based on the MR data, by applying a complex conjugate to the phase data (hereinafter, "second multiplied phase data") having the phase angles obtained by multiplying the phase angles in the unwrapped phase data by 1/(2n). When the second multiplied phase data is expressed as $\exp(i\theta)$, the correction map generating function 157 is configured to generate the phase correction map expressed as $\exp(-i\theta)$, by applying the process of realizing the complex conjugate to $\exp(i\theta)$.

By employing the image generating function 159, the processing circuitry 15 is configured to generate the complex image having the complex signal on the basis of the MR data. More specifically, the image generating function 159 is configured to generate the complex image by performing a Fourier transform on the MR data. The generated complex image will be used for generating the phase data. In that situation, the phase data may be generated by the image generating function 159.

The image generating function 159 is configured to perform a phase correction on the MR data by using the phase correction map. In that situation, the image generating function 159 corresponds to a phase correcting function. The processing circuitry 15 realizing the phase correcting function configured to perform the phase correction corresponds to a phase correcting unit. On the basis of the complex image and the phase correction map, the image generating function 159 is configured to generate a phase-corrected complex image obtained by correcting the phase of the complex signal related to the complex image. More specifically, the image generating function 159 is configured to generate the phase-corrected complex image by multiplying the complex image by the phase correction map. The image generating function 159 is configured to generate a real part image of the phase-corrected complex image, on the basis of the phase-corrected complex image. Because the process of generating the real part image from the phase-corrected complex image is the same as the process of generating a real image from a complex image, explanations thereof will be omitted. The image generating function 159 is configured to store the generated real part image into the memory 13.

For example, the input/output interface 17 includes: an input interface configured to receive various types of instructions and inputs of information from the operator; and an output interface configured to output various types of information. The input interface is realized by using, for example, a trackball, a switch button, a mouse, a keyboard, a touchpad on which input operations can be performed by touching an operation surface thereof, a touch screen in which a display screen and a touchpad are integrally formed, contactless input circuitry using an optical sensor, audio input circuitry, and/or the like. The input interface is connected to the processing circuitry 15 and is configured to convert an input operation received from the operator into an electrical signal and to output the electrical signal to the processing circuitry 15.

In the present disclosure, the input interface does not necessarily have to include physical operation component parts such as a mouse, a keyboard, and/or the like. For instance, possible examples of the input interface include electrical signal processing circuitry configured to receive an electrical signal corresponding to an input operation from an external input machine provided separately from the MRI apparatus 100 and to output the electrical signal to controlling circuitry.

The output interface is realized by a display, for example. Under control of the processing circuitry 15 or the system controlling circuitry 123, the display is configured to display various types of Graphical User Interfaces (GUIs), the MR image generated by the processing circuitry 15, and the like. Further, the display is configured to display image taking parameters related to scans, various types of information related to image processing, and the like. For example, the display is realized by using a display mechanism such as a Cathode Ray tube (CRT) display, a liquid crystal display, an organic electroluminescence (EL) display, a Light Emitting Diode (LED) display, a plasma display, or other arbitrary displays and monitors known in the relevant technical field.

The process (hereinafter, "phase correcting process") of correcting the phase performed by the MRI apparatus 100 according to the present embodiment configured as described above will be explained with reference to FIGS. 5 to 7. The phase correcting process is a process of performing the phase correction on the complex image based on the MR data acquired by implementing the IR method under the $\pi$ condition. As a result of the phase correcting process, the phase difference caused by the difference in the longitudinal magnetization relaxation time T1 between the two or more observed elements is corrected.

Figure 5:
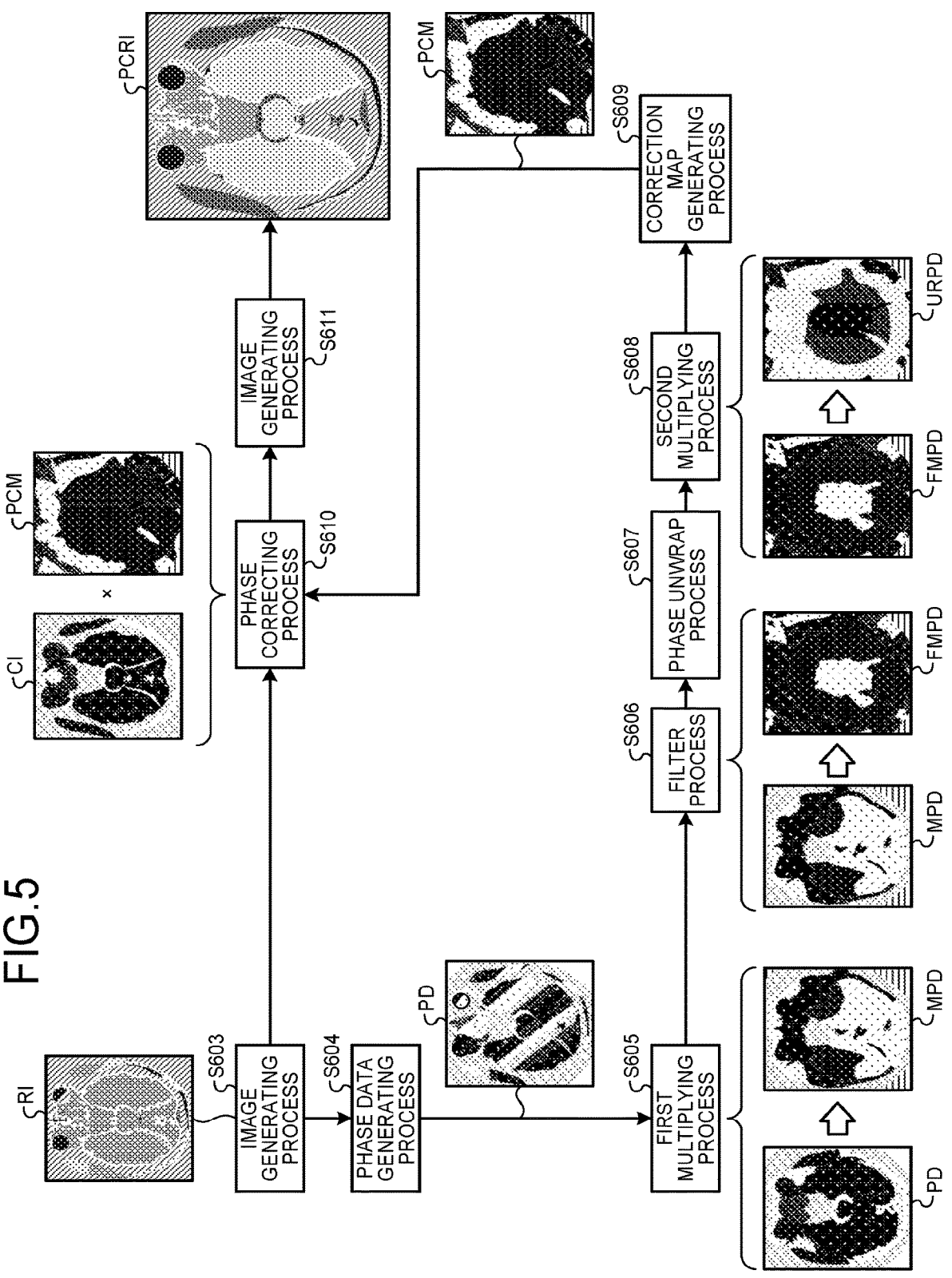
FIG. 5 is a chart illustrating an outline of a phase correcting process according to the embodiment.
Figure 6:
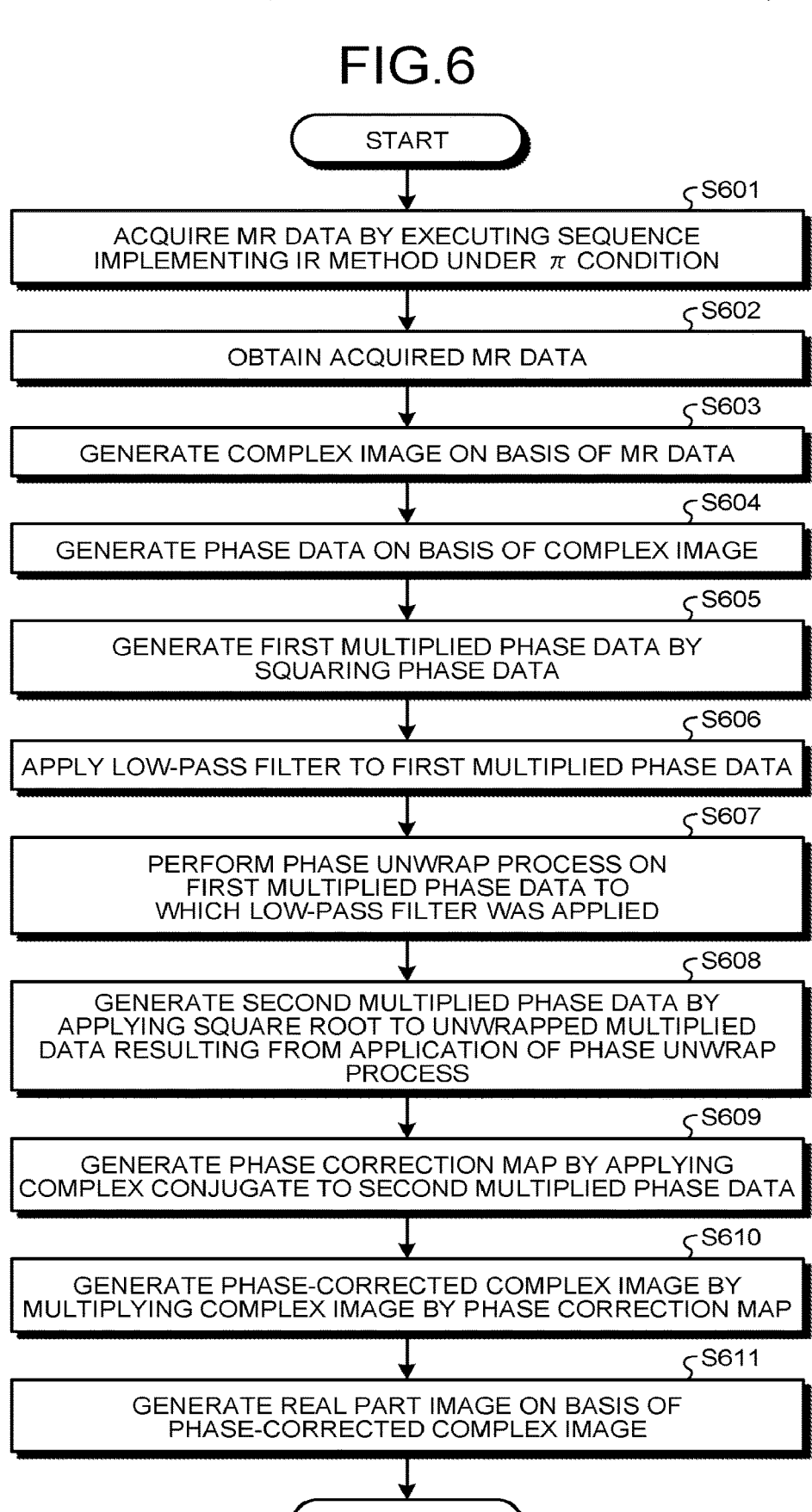
FIG. 6 is a flowchart according to the embodiment illustrating an example of a procedure in the phase correcting process.
Figure 7:
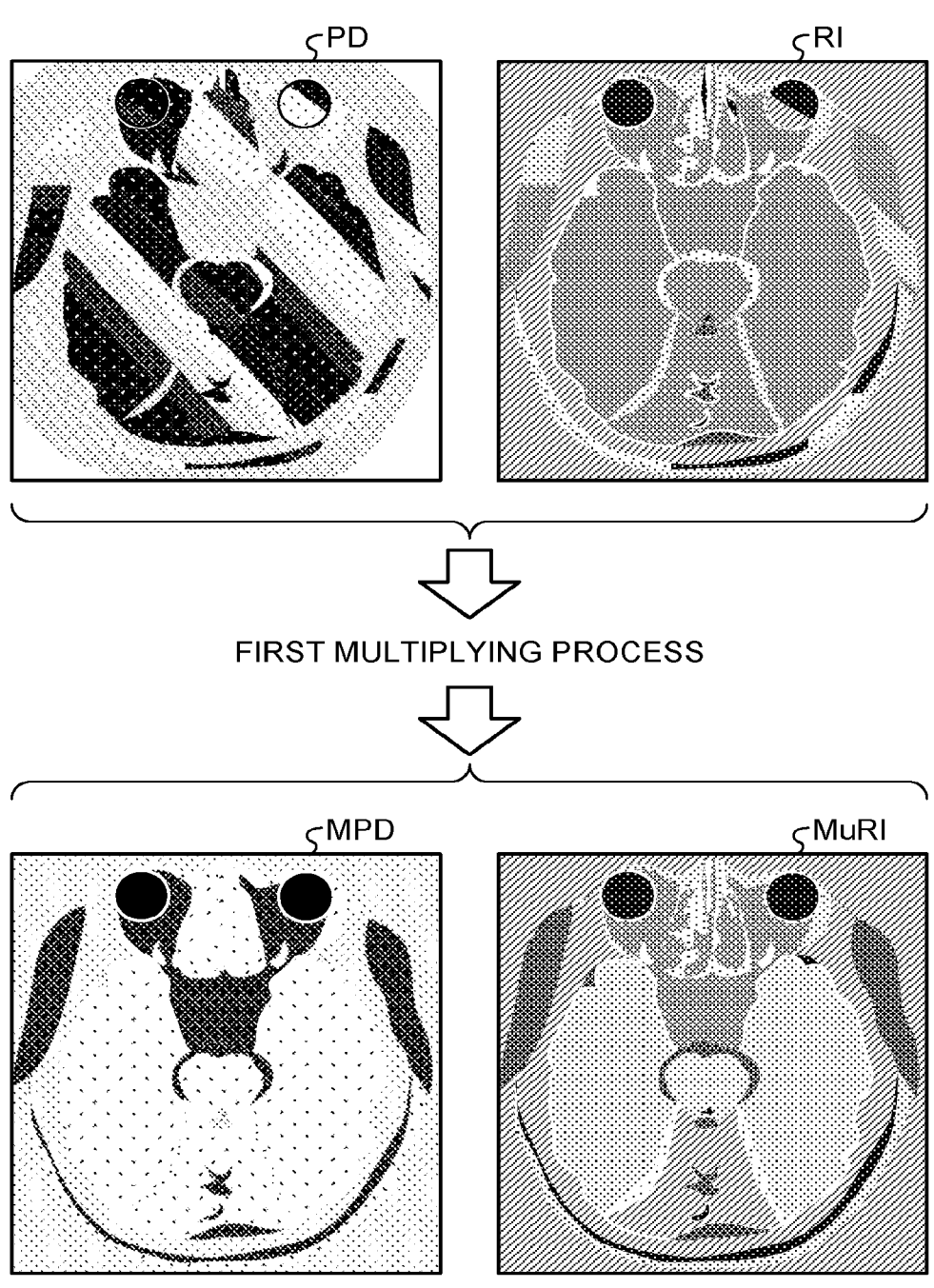
FIG. 7 is a drawing according to the embodiment illustrating examples of differences between phase data and a real image observed before and after a first multiplying process.

FIG. 5 is a chart illustrating an outline of the phase correcting process. FIG. 6 is a flowchart illustrating an example of a procedure in the phase correcting process. FIG. 7 is a drawing illustrating examples of differences between phase data and a real image observed before and after the first multiplying process performed by the first multiplying function 1531. Prior to the execution of the phase correcting process, when images elements include the inner ear, for example, according to an instruction from the operator received via the input/output interface 17 or examination order information received via the communication interface 11, CSF and WM are set as observed elements. Accordingly, the imaging controlling circuitry 121 is configured to set the $\pi$ condition.

Phase Correcting Process

Step S601:

The imaging controlling circuitry 121 images the patient P by implementing the IR method under the set $\pi$ condition. Thus, the imaging controlling circuitry 121 acquires MR data.

Step S602:

By employing the obtaining function 150, the processing circuitry 15 obtains the MR data acquired by implementing the IR method under the $\pi$ condition. The obtaining function 150 stores the obtained MR data into the memory 13.

Step S603:

By employing the image generating function 159, the processing circuitry 15 generates the complex image by performing the Fourier transform on the MR data. The image generating function 159 stores the generated complex image into the memory 13. In this situation, the image generating function 159 may generate a real image on the basis of the complex image. As illustrated in FIGS. 5 and 7, a real image RI exhibits a stripe pattern caused by a phase change.

Step S604:

By employing the phase data generating function 151, the processing circuitry 15 generates phase data on the basis of the complex image. As illustrated in FIGS. 5 and 7, the phase data PD exhibits a stripe pattern caused by a phase change and non-contiguous dark/light areas representing a phase difference caused by a positivity/negativity difference in phase angles between CSF and WM (see FIG. 3).

Step S605:

By employing the first multiplying function 1531, the processing circuitry 15 generates the first multiplied phase data MPD, by squaring the phase data PD. As illustrated in FIG. 7, the positivity/negativity difference in the phase angles is mitigated between the first multiplied phase data MPD generated from the multiplying process by the first multiplying function 1531 and a real part image MuRI after the multiplying process.

Step S606:

By employing the phase unwrap function 155, the processing circuitry 15 applies a low-pass filter to the first multiplied phase data MPD. As a result, noise of the radio frequency component of the first multiplied phase data MPD illustrated in FIG. 5 is reduced. By applying the low-pass filter to the first multiplied phase data MPD, the phase unwrap function 155 generates multiplied phase data (hereinafter, "filtered multiplied data") FMPD in which the noise of the radio frequency has been reduced. Alternatively, the application of the low-pass filter to the first multiplied phase data MPD may be realized by another function such as the first multiplying function 1531 or the image generating function 159.

Step S607:

By employing the phase unwrap function 155, the processing circuitry 15 performs the phase unwrap process on the first multiplied phase data to which the low-pass filter was applied. In other words, the phase unwrap function 155 unfolds the phase of the filtered multiplied data, by applying the phase unwrap process to the filtered multiplied data having the phase angles multiplied by 2n.

Step S608:

By employing the second multiplying function 1532, the processing circuitry 15 multiplies the phase angles in the unfolded phase data by 1/(2n). More specifically, the second multiplying function 1532 generates second multiplied phase data URPD, by applying the square root to the unwrapped multiplied data resulting from the phase unwrap process. As a result, the phase angles in the second multiplied phase data URPD has returned to the same phase angles as those in the phase data PD. In this situation, the phase angle of CSF after being multiplied by 2n is equal to $2\theta$, as illustrated in FIG. 4. Consequently, the phase angles of CSF and WM after the second multiplying process are equal to each other.

Step S609:

By employing the correction map generating function 157, the processing circuitry 15 generates a phase correction map PCM by performing a complex conjugate process (a correction map generating process) on the second multiplied phase data URPD. As illustrated in FIG. 5, in the phase correction map PCM, the noise has been reduced, while the phase angles in the phase data are in the opposite phase.

Step S610:

By employing the image generating function 159, the processing circuitry 15 generates the phase-corrected complex image by multiplying a complex image CI by the phase correction map PCM. The phase-corrected complex image is an image in which the dark/light unevenness caused by the phase difference has been reduced, in comparison to the complex image generated on the basis of the MR data.

Step S611:

By employing the image generating function 159, the processing circuitry 15 generates a real part image PCRI on the basis of the phase-corrected complex image. As illustrated in FIG. 5, in the real part image PCRI resulting from the application of the phase correcting process, cyclic dark/light areas (phase unevenness) and the dark/light areas caused by the phase difference between CSF and WM have been reduced in comparison to the real part image prior to the application of the phase correcting process.

The MRI apparatus 100 according to the embodiment described above is configured to acquire the MR data by implementing the inversion recovery method, under the condition where the phase difference in the complex signal related to the two or more observed elements is equal to $\pi$, due to the difference in the longitudinal magnetization relaxation time related to the two or more observed elements. As a result, the MRI apparatus 100 according to the embodiment is able to acquire the MR data in which the phase difference in the complex signal is equal to r with respect to the two or more observed elements. Consequently, the MRI apparatus 100 in the present example is able to effectively perform the phase correcting process and is thus able to excellently eliminate a background phase from the real part image related to diagnosing processes on the inner ear or the like, for example.

Further, the MRI apparatus 100 according to an embodiment is configured: to obtain the MR data acquired by implementing the inversion recovery method, under the condition where the phase difference in the complex signal related to two or more observed elements is equal to $\pi$, due to the difference in the longitudinal magnetization relaxation time related to the two or more observed elements; to generate at least the phase data PD on the basis of the MR data; to multiply the phase angles in the phase data PD by 2n (where n is a natural number); to unfold the phase of the phase data (the first multiplied phase data MPD) having the phase angles multiplied by 2n; to multiply the phase angles in the unfolded phase data (the unwrapped multiplied data) by 1/(2n); to generate the phase correction map PCM used for correcting the phase with respect to the complex signal related to the complex image based on the MR data, by applying the complex conjugate to the phase data (the second multiplied phase data) URPD having the phase angles multiplied by 1/(2n); and to perform the phase correction on the MR data by using the phase correction map.

For example, by performing the phase unwrap process on the phase data (the filtered multiplied data) FMPD obtained by applying the low-pass filter to the phase data (the first multiplied phase data) MPD multiplied by 2n, the MRI apparatus 100 according to an embodiment is configured to unfold the phase of the filtered multiplied data FMPD. Further, on the basis of the complex image CI and the phase correction map PCM, the MRI apparatus 100 according to an embodiment is configured to generate the phase-corrected complex image in which the phase of the complex signal related to the complex image CI has been corrected and to further generate the real part image PCRI of the phase-corrected complex image on the basis of the phase corrected complex image.

With the configurations described above, the MRI apparatus 100 according to the embodiment is able to perform the phase correction on the MR image, without using a template image. Consequently, the MRI apparatus 100 according to the present embodiments is able to shorten imaging periods and is thus able to reduce burdens of medical examinations imposed on the patient P and the operator and to improve a throughput of the medical examinations. Furthermore, the MRI apparatus 100 according to the embodiments is able to perform the phase correction on the MR image conveniently with a high level of precision, without the need to optimize the threshold value related to the masking process.

As explained above, the MRI apparatus 100 according to the embodiments is able to generate the phase-corrected MR image in a short period of time in an excellent manner, in relation to imaged elements including, for example, CSF and WM/GM; a normal myocardium and a damaged myocardium; WM, GM, and fat; or the like.

In a modification example of the present embodiment, technical concept of the present embodiment may be realized by the image processing apparatus 1. In that situation, by employing the obtaining function 150 of the processing circuitry 15, the image processing apparatus 1 is configured to obtain MR data from an MRI apparatus. The MR data is MR data acquired by implementing the IR method under the π condition. The processing procedure in the phase correcting process performed by the image processing apparatus 1 is obtained by eliminating the process at step S601 from the flowchart in FIG. 6. Because the procedure in the other processes and advantageous effects thereof are the same as those of the embodiment, explanations thereof will be omitted.

When the technical concept of the embodiment is realized by a phase correcting method, the phase correcting method includes: obtaining MR data acquired by implementing the inversion recovery method under the condition where the phase difference in the complex signal related to two or more observed elements is equal to π, due to the difference in the longitudinal magnetization relaxation time between the two or more observed elements; generating at least the phase data PD on the basis of the MR data; multiplying the phase angle in the phase data by 2n (where n is a natural number); unfolding the phase of phase data having the phase angle multiplied by 2n; multiplying the phase angle in the unfolded phase data by 1/(2n); generating the phase correction map PCM used for correcting the phase with respect to the complex signal, by applying the complex conjugate to the phase data having the phase angle multiplied by 1/(2n); and performing the phase correction on the MR data by using the phase correction map PCM. Because the procedure in the phase correcting process related to the present phase correcting method and advantageous effects thereof are the same as those of the embodiment, explanations thereof will be omitted.

When the technical concept of the embodiment is realized as a phase correction program, the phase correction program causes the computer to realize: obtaining MR data acquired by implementing the inversion recovery method under the condition where a phase difference related to two or more observed elements is equal to π, due to the difference in the longitudinal magnetization relaxation time between the observed elements; generating at least the phase data PD on the basis of the obtained MR data; multiplying a phase angle in the generated phase data PD by 2n (where n is a natural number); unfolding the phase of phase data (the first multiplied phase data) MPD having the phase angle multiplied by 2n; multiplying the phase angle in the unfolded phase data by 1/(2n); generating the phase correction map PCM used for correcting the phase with respect to a complex signal, by applying the complex conjugate to the phase data (the second multiplied phase data) URPD having the phase angle multiplied by 1/(2n); and performing the phase correction on the MR data by using the phase correction map PCM.

For example, it is also possible to realize the phase correcting process by installing the phase correction program into a computer of a modality such as the MRI apparatus 100, a PACS server, or any of various types of image processing servers and further loading the program into a memory. In that situation, it is also possible to distribute the program capable of causing the computer to implement the method, as being stored in a storage medium such as a magnetic disk (e.g., a hard disk), an optical disc (e.g., a CD-ROM, a DVD), or a semiconductor memory. Because the procedure in the phase correcting process realized by the phase correction program and advantageous effects thereof are the same as those of the embodiment, explanations thereof will be omitted.

Further, when the technical concept of the embodiment is realized as an imaging controlling method, the imaging controlling method includes: acquiring magnetic resonance data by implementing the inversion recovery method under the condition where the phase difference in the complex signal related to two or more observed elements is equal to π, due to the difference in longitudinal magnetization relaxation time between the two or more observed elements. Because the procedure in the imaging process realized by the imaging controlling method and advantageous effects thereof are the same as those of the embodiment, explanations thereof will be omitted.

According to at least one aspect of the embodiments and the like described above, it is possible to acquire the magnetic resonance data on which it is possible to properly perform the phase correction. Consequently, according to at least one aspect of the embodiments and the like, it is possible to properly carry out the phase correction.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
a transmission coil configured generate a radio frequency pulse corresponding to a radio frequency magnetic field;
a reception coil configured to receive a magnetic resonance signal emitted from a patient due to the radio frequency magnetic field;
processing circuitry configured:
to obtain magnetic resonance data acquired from the magnetic resonance signal by implementing an inversion recovery method under a condition where a phase difference in a complex signal related to two or more observed elements is equal to $\pi$, due to a difference in longitudinal magnetization relaxation time between the two or more observed elements;
to generate at least phase data on a basis of the magnetic resonance data;
to multiply a phase angle in the phase data by 2n (where n is a natural number);
to unfold a phase of phase data having the phase angle multiplied by 2n;
to multiply a phase angle in the unfolded phase data by 1/(2n);
to generate a phase correction map used for correcting a phase with respect to the complex signal, by applying a complex conjugate to phase data having the phase angle multiplied by 1/(2n); and
to perform a phase correction on the magnetic resonance data by using the phase correction map.

2. The magnetic resonance imaging apparatus according to claim 1, wherein the processing circuitry is configured to unfold a phase of phase data obtained by applying a low-pass filter to the phase data having the phase angle multiplied by 2n.

3. The magnetic resonance imaging apparatus according to claim 1, wherein the processing circuitry is configured:
to generate a complex image having the complex signal on a basis of the magnetic resonance data;
to generate a phase-corrected complex image in which the phase of the complex signal has been corrected, on the basis of the complex image and the phase correction map; and
to generate a real part image of the phase-corrected complex image, on a basis of the phase-corrected complex image.

4. A phase correcting method comprising:
generating, with a transmission coil, a radio frequency pulse corresponding to a radio frequency magnetic field;
receiving, by a reception coil, a magnetic resonance signal emitted from a patient due to the radio frequency magnetic field;
obtaining magnetic resonance data acquired by implementing an inversion recovery method under a condition where a phase difference in a complex signal related to two or more observed elements is equal to x, due to a difference in longitudinal magnetization relaxation time between the two or more observed elements;
generating at least phase data on a basis of the magnetic resonance data;
multiplying a phase angle in the phase data by 2n (where n is a natural number);
unfolding a phase of phase data having the phase angle multiplied by 2n;
multiplying a phase angle in the unfolded phase data by 1/(2n);
generating a phase correction map used for correcting a phase with respect to the complex signal, by applying a complex conjugate to phase data having the phase angle multiplied by 1/(2n); and
performing a phase correction on the magnetic resonance data by using the phase correction map.

* * * * *